(12) United States Patent
Sherman et al.

(10) Patent No.: US 8,874,035 B2
(45) Date of Patent: Oct. 28, 2014

(54) APPARATUS, SYSTEM AND METHOD FOR MONITORING AND MAINTAINING CRITICAL MEDICAL EQUIPMENT

(75) Inventors: Leslie H. Sherman, Denville, NJ (US); George Beck, Mendham, NJ (US); Denise Eizadkhah, Bridgewater, NJ (US); Dorian LeCroy, New York, NY (US)

(73) Assignee: Impact Instrumentation, Inc., West Caldwell, NJ (US)

( * ) Notice: Subject to any disclaimer, the term of this patent is extended or adjusted under 35 U.S.C. 154(b) by 210 days.

(21) Appl. No.: 12/830,808

(22) Filed: Jul. 6, 2010

(65) Prior Publication Data

US 2011/0009061 A1 Jan. 13, 2011

Related U.S. Application Data

(60) Provisional application No. 61/223,465, filed on Jul. 7, 2009.

(51) Int. Cl.
*H04B 7/00* (2006.01)
*G06Q 50/22* (2012.01)
*G06F 19/00* (2011.01)

(52) U.S. Cl.
CPC ............ *G06Q 50/22* (2013.01); *G06F 19/3412* (2013.01)
USPC .............................. 455/41.2; 174/59; 702/114

(58) Field of Classification Search
CPC .................................................... G06F 19/3412
USPC .............................. 455/41.2; 174/59; 702/114
See application file for complete search history.

(56) References Cited

U.S. PATENT DOCUMENTS

2007/0049842 A1* 3/2007 Hill et al. ...................... 600/534
2007/0255116 A1* 11/2007 Mehta et al. .................. 600/300
2008/0065264 A1* 3/2008 Omura et al. ................. 700/231

* cited by examiner

*Primary Examiner* — Hsin-Chu Liao
(74) *Attorney, Agent, or Firm* — Gerald E. Hespos; Michael J. Porco; Matthew T. Hespos

(57) ABSTRACT

An apparatus, system and method for maintaining critical medical equipment for stockpile applications are provided. The apparatus, system and method of the present disclosure can be used to monitor and maintain critical medical equipment in a continuous state of readiness. The apparatus includes a storage case which protects a medical device disposed therein and the accessories required for its immediate application while also providing for constant or intermittent charging of the device's internal battery and serial data monitoring of the primary systems. The system and method also incorporate design features in the medical device which enable performance testing via a remote interface while the device is secured within the storage case.

17 Claims, 1 Drawing Sheet

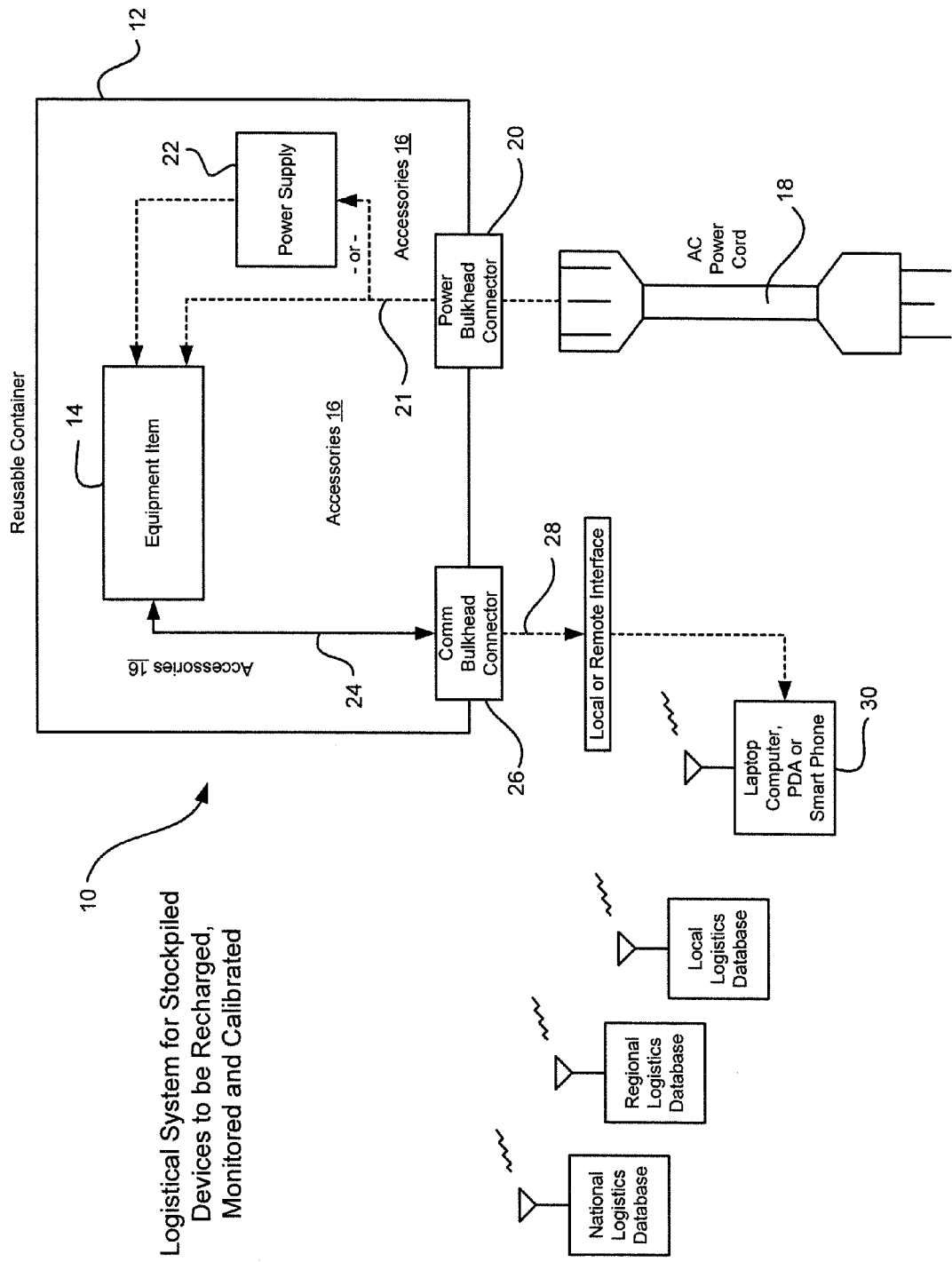

APPARATUS, SYSTEM AND METHOD FOR MONITORING AND MAINTAINING CRITICAL MEDICAL EQUIPMENT

This application claims priority on U.S. Provisional Application No. 61/223,465 filed on Jul. 7, 2009, entitled "METHOD AND APPARATUS FOR MONITORING AND MAINTAINING CRITICAL MEDICAL EQUIPMENT", the contents of which are hereby incorporated by reference in their entirety.

BACKGROUND

1. Field

The present disclosure relates generally to medical systems, and more particularly, to an apparatus, system and method for monitoring and maintaining critical medical equipment for stockpile applications.

2. Description of the Related Art

The potential for mass casualty events whether natural or manmade has resulted in the Federal Government as well as state and local governments stockpiling medical supplies and equipment. Stockpiling of sophisticated medical equipment presents significant challenges given the need to maintain rechargeable batteries associated with the equipment at usable levels. In addition, given the critical nature or their use, these devices also require routine maintenance checks to assure they are ready to operate when required.

Current practice requires an equipment case which housed the equipment to be opened on a regular basis. This allows access to the device so that its internal batteries may be recharged. In addition to being labor intensive, maintaining the integrity of the medical equipment and its supplies as a set is critical. In addition, equipment items must be removed from their reusable containers for calibration and operational testing purposes. This typically requires removal of accessories and support supplies from the container and, to expedite processing, it is common practice to do so with multiple devices at the same time. An unsecured reusable container presents a risk that parts of the supply kit may become compromised due to handling, borrowing or pilferage. This risk is greatly increased as more devices are processed at the same time.

In some instances, storage cases have been developed a with power connector which allows the device to be always connected while awaiting the application of external power. When external power is applied to the storage case connector, it allows for constant or intermittent battery charging.

For those devices that can be recharged through a storage case connector, this capability has three major shortcomings that can provide a false sense of security and compromise the ability to deploy and operate these items when needed.

First, warehouse conditions for stockpiled supplies and equipment can range from temperature and humidity controlled environments to uncontrolled environments where temperature and humidity levels can go beyond the battery manufacturers specifications. These extremes can exceed the temperature ranges required to properly charge equipment batteries and, in some temperature extremes, the battery recharging process actually stops.

Second, battery technology is such that a given battery's actual life expectancy cannot be readily determined when stockpiled. Recharging batteries as described above provides no feedback to the logistician whether the battery has been fully charged, partially charged or is defective.

And third, there will still come a time when the case must be opened to perform calibration and operational testing. When this occurs, it once again presents the risk that parts of the supply kit may become compromised due to handling, borrowing or pilferage. Again, this risk is greatly increased as more devices are processed at the same time.

Despite their ability to charge the medical device, these approaches and systems fundamentally require that the storage case be opened to expose the device and operationally check it to assure that the device is ready to operate and to confirm the charge state of the battery. This practice risks damaging the device and/or accessories or omitting accessories when the kit is repackaged. It is also labor intensive and requires a level of training in the maintenance personnel that must be sustained in addition to the equipment. The inherent requirement of trained personnel also limits stockpiling to locations with trained personnel. Finally, current management continuously risks compromising the medical device as there are minimal controls once the case is opened no matter the environment or circumstance.

Therefore, a need exists for techniques to monitor and maintain critical medical equipment that is being stockpiled without having to access or disturb each piece of medical equipment.

SUMMARY

An apparatus, system and method for maintaining critical medical equipment for stockpile applications are provided. The apparatus, system and method of the present disclosure can be used to monitor and maintain critical medical equipment in a continuous state of readiness. The apparatus includes a storage case which protects a medical device disposed therein and the accessories required for its immediate application while also providing for constant or intermittent charging of the device's internal battery and serial data monitoring of the primary systems. The system and method also incorporate design features in the medical device which enable performance testing via a remote interface while the device is secured within the storage case.

According to one aspect of the present disclosure, an apparatus is provided including a storage case for storing at least one medical device; an external power connector disposed on a surface of the storage case for providing power to the at least one medical device without opening of the case, the external power connector being coupled to the at least one medical device via a first cable; and a data communication connector disposed on the surface of the storage case for communicating data from the at least one medical device to an external computing device, the data communication connector being coupled to the at least one medical device via a second cable.

In one aspect, the data communication connector is a USB connector or a RS232 connector.

If a further aspect, the data communication connector is a wireless connector, e.g., a WiFi transceiver, a Bluetooth transceiver, a cellular transceiver, etc.

According to another aspect of the present disclosure, a system for monitoring and maintaining critical medical equipment is provided including at least one apparatus comprising: a storage case for storing at least one medical device; an external power connector disposed on a surface of the storage case for providing power to the at least one medical device without opening of the case, the external power connector being coupled to the at least one medical device via a first cable; and a data communication connector disposed on the surface of the storage case for communicating data from the at least one medical device to an external computing device, the data communication connector being coupled to the at least one medical device via a second cable; and the external computing device for determining a state of readiness of the at least one medical device.

In yet a further aspect, the external computing device is configured to simulate operation of the at least one medical device, calibrate the at least one medical device, cycle an internal battery of the at least one medical device to optimize the battery's life expectancy, generate an alert upon failure of the at least one medical device and store at least one monitored parameter of the at least one medical device in a database.

According to another aspect of the present disclosure, a method for monitoring and maintaining critical medical equipment is provided including providing at least one apparatus comprising: a storage case for storing at least one medical device; an external power connector disposed on a surface of the storage case for providing power to the at least one medical device without opening of the case, the external power connector being coupled to the at least one medical device via a first cable; and a data communication connector disposed on the surface of the storage case for communicating data from the at least one medical device to an external computing device, the data communication connector being coupled to the at least one medical device via a second cable; and determining a state of readiness of the at least one medical device by the external computing device.

BRIEF DESCRIPTION OF THE DRAWING

The above and other aspects, features, and advantages of the present disclosure will become more apparent in light of the following detailed description when taken in conjunction with the accompanying drawings.

FIG. 1 is a diagram of an exemplary system for monitoring and maintaining stockpiled critical medical equipment in accordance with an embodiment of the present disclosure.

To facilitate understanding, the images in the drawings are simplified for illustrative purposes and are not depicted to scale.

The appended drawings illustrate exemplary embodiments of the present disclosure and, as such, should not be considered as limiting the scope of the disclosure that may admit to other equally effective embodiments. Correspondingly, it has been contemplated that features or steps of one embodiment may beneficially be incorporated in other embodiments without further recitation.

In some embodiments, particular method steps of the discussed methods are performed in the depicted order. In alternate embodiments, in the respective methods, at least two method steps or portions thereof may be performed contemporaneously, in parallel, or in a different order.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its spirit and scope.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage, programmable logic or other device or devices.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

The word "exemplary" is used herein to mean "serving as an example, instance, or illustration." Any configuration or design described herein as "exemplary" is not necessarily to be construed as preferred or advantageous over other configurations or designs. Herein, the phrase "coupled with" is defined to mean directly connected to or indirectly connected with through one or more intermediate components. Such intermediate components may include both hardware and software based components.

Referring to FIG. 1, an apparatus 10 for monitoring and maintaining stockpiled critical medical equipment is provided. The apparatus includes a storage case 12 which protects a critical medical device or devices 14 and the required accessories and consumables 16 used for immediate application of the device 14 in the event of a medical emergency. The storage case 12 provides a connection for both external power and serial data communication (wired or wireless) to the medical device(s) on a surface of the case so the case does not have to be opened to charge or monitor the medical device disposed therein. Inherent in the medical device's design is the ability to communicate with its internal systems (e.g., battery controller, processors, sensors, etc) via serial data while the device's primary power control is in the off position. This method enables the internal battery of the device to remain charged and enables critical operating components to be monitored continuously or intermittently to assure the readiness of the device to operate in an emergency.

The apparatus includes elements that: permit connection to an external source of power that is compatible with the equipment item, e.g., an AC power cord 18; a power bulkhead connector 20 that is capable of connection to the external source of power and to further connect it either directly to the equipment item 14 or through a separate power supply module 22 and then to the equipment item external power input connector; the equipment item communications port to a communications cable 24 having its distal end connected to a communications port bulkhead connector 26; from the communications port bulkhead connector 26 to one end of a communications cable 28; and the other end of the communications cable to an external programmable device 30 such as a portable computer, personal digital assistant or smart phone.

On one embodiment, the apparatus 10 includes an equipment item 14 stored in a reusable container 12 with its accessories and supplies 16, and allows it to be rapidly deployed during an emergency or crisis event. It is to be appreciated that the case or container 12 includes at least one surface for supporting the connectors. Furthermore, the case 12 includes an openable portion which may include a locking mechanism.

Depending upon the equipment item 14 stored with the case 12, it may be necessary to store it with an interfacing fixture whose complexity determines the level of tests and measurements that can be applied to it. External power is applied through an extension cord 18 to a bulkhead mounted power connector 20 attached to a surface of the reusable container 12 so it can be accessed without opening the case/container 12. Inside the reusable container 12 and electrically attached and appropriately insulated, is a wire pigtail 21 that terminates in a power plug. The power plug attaches into the power inlet socket of the equipment item or inlet socket of a separate power supply module 22. If the equipment item 14 is used with a separate power supply module 22, the module's output cable plug is attached into the equipment item's power inlet socket.

A bulkhead communications connector 26 is mounted to the surface of reusable container 12. Inside the reusable container 12 and electrically attached and appropriately insulated, is a wire pigtail 24 that terminates in a bidirectional digital communication plug, typically of the USB or RS232 type. The communication plug is connected to the equipment item's communications port. An external computing device 30 such as a laptop computer, a personal digital assistant (PDA) or a smart phone containing test, calibration, memory space and communications software and hardware is cable-attached to the bulkhead communications connector 26. Alternatively, the external computing device 30 is coupled to the communications connector 26 via a wireless connection, as described below.

Communications, between the medical device or item disposed in the case/container 12 and the external computing device 30, may be accomplished via wired or wireless connections. The hardwire connection may include but is not limited to hard wire cabling e.g., parallel or serial cables, RS232, RS485, USB cable, Firewire (1394 connectivity) cables, Ethernet, Fiber Optic, Fiber Optic over Ethernet, and the appropriate communication port configuration. The wireless connection includes a transceiver that will operate under any of the various known wireless protocols including but not limited to Bluetooth™ interconnectivity, infrared connectivity, cellular connectivity, radio transmission connectivity including computer digital signal broadcasting and reception commonly referred to as Wi-Fi or 802.11.X (where x denotes the type of transmission), satellite transmission or any other type of communication protocols, communication architecture or systems currently existing or to be developed for wirelessly transmitting data including spread spectrum 900 MHz, or other frequencies, Zigbee (i.e., systems compliant with the IEEE 802.15.4 standard for wireless personal area networks wireless (WPANs)), WiFi, or any mesh enabled wireless communication.

The apparatus 10 may communicate to the computing device 30 or other computing device via a communications module over a communication network. The apparatus 10 may be connected to the communication network, e.g., the Internet, by any known means, for example, a hardwired or wireless connection. It is to be appreciated that the communication network may be a local area network (LAN), wide area network (WAN), the Internet or any known network that couples devices to enable various modes of communication via network messages. Furthermore, the apparatus 10 will communicate using the various known protocols such as Transmission Control Protocol/Internet Protocol (TCP/IP), File Transfer Protocol (FTP), Hypertext Transfer Protocol (HTTP), etc. and secure protocols such as Internet Protocol Security Protocol (IPSec), Point-to-Point Tunneling Protocol (PPTP), Secure Sockets Layer (SSL) Protocol, etc.

In a typical use of the system shown in FIG. 1, the operator would attach the external power cord 18 to the storage case 12 which would initiate charging of the medical device's internal batteries for some predetermined period of time. Following charging, the operator would establish bidirectional serial communication with the medical device using a computing device 30 such as an external computer, personal digital assistant (PDA) or smart phone. The computer, PDA or smart phone would run diagnostic software that would query the device's internal systems. A comprehensive system check would begin where the device is identified by serial number along with data regarding the current hardware and software configuration of the device. Once the identity and configuration where ascertained, the software being executed on an appropriate processor of the external computing device 30 would then prompt the device 14 to perform system checks of processors and sensors. In addition, the software would simulate operation of the medical device or item 14 by operating key functional components or measuring the performance against reference loads attached to operating interfaces of the device 14. Information generated during the various checks may be transmitted and stored in a local, regional, or national logistics database by the computing device 30.

The apparatus, system and method of the present disclosure provide several advantageous features. The apparatus, system and method provide automatic or semi-automatic control of the equipment item to conduct battery status and calibration status checks, calibrations, operational checks, and alarm checks, while the equipment item 14 is stowed in its reusable container 12. The techniques of the present disclosure reduce labor costs and personnel time in comparison to manual processes. The labor component can be virtually eliminated based on the level of automation implemented. The level of automation can be determined by software that schedules various processes to initiate at chosen intervals.

The apparatus, system and method of the present disclosure maintain stockpiled equipment at a high state of readiness. Equipment items can remain palletized and ready-for-shipment. Additionally, the techniques of the present disclosure can help optimize battery life expectancy. Maintaining batteries at full capacity for long intervals of time can actually decrease their useful life. The apparatus, system and method can cycle and recharge batteries or maintain "smart" batteries at less-than-full capacity levels and thereby maximize life expectancy.

Furthermore, logistical security is maintained. There is no need to open the reusable container unless monitoring software detects an anomaly or failure and alerts the logistician who can then deploy appropriate maintenance personnel. The apparatus, system and method can support interoperability with local, regional and national asset databases. Individual equipment items can be tracked and their operational status and history queried at anytime.

In another aspect of the present disclosure, the apparatus, system and method can support data mining and facilitate trend analyses for quality assurance assessments. Individual equipment items can be compared against their peers, and entire equipment populations can be polled to determine reliability statistics.

In yet another aspect, the apparatus, system and method can support testing of equipment items to various levels of performance both with and without fixtures. Specific fixtures can be connected to the equipment item and remain inside its reusable container. The complexity of these fixtures can vary based on the available space within the container and the degree of testing that is required.

Although the disclosure herein has been described with reference to particular illustrative embodiments, it is to be understood that these embodiments are merely illustrative of the principles and applications of the present disclosure. Therefore numerous modifications may be made to the illustrative embodiments and other arrangements may be devised without departing from the spirit and scope of the present disclosure.

What is claimed is:

1. An apparatus for monitoring and maintaining medical devices stockpiled for emergency use, comprising:
   a storage case;
   at least one electrically powered medical device in the storage case, the electrically powered medical device in the storage case including a rechargeable battery and at least one processor;
   an external power connector disposed on a surface of the storage case for providing power to the at least one medical device without opening of the case, the external power connector being coupled to the at least one medical device via a first cable and being configured for recharging the battery; and
   a data communication connector disposed on the surface of the storage case for communicating data from the at least one medical device to an external computing device, the data communication connector being coupled to the at least one medical device via a second cable and being configured for: determining a charged state of the battery, prompting the medical device to perform system checks of the at least one processor and simulating operation of the medical device by operating at least one component of the medical device.

2. The apparatus of claim 1, further comprising a power supply module disposed in the storage case, wherein the power supply module is coupled between the external power connector and the at least one medical device.

3. The apparatus of claim 1, wherein the data communication connector is a USB connector.

4. The apparatus of claim 1, wherein the data communication connector is a RS232 connector.

5. The apparatus of claim 1, wherein the data communication connector is a wireless connector.

6. The apparatus of claim 1, wherein the data communication connector is a WiFi transceiver.

7. The apparatus of claim 1, wherein the data communication connector is a Bluetooth transceiver.

8. The apparatus of claim 1, wherein the data communication connector is a cellular transceiver.

9. A system for monitoring and maintaining critical medical equipment stockpiled for emergency use, comprising:
   at least one apparatus comprising:
   a storage case;
   at least one electrically powered medical device in the storage case, the medical device having at least one processor and at least one rechargeable battery;
   an external power connector disposed on a surface of the storage case for providing power to the at least one medical device without opening of the case, the external power connector being coupled to the at least one medical device via a first cable and being configured for recharging the battery; and
   a data communication connector disposed on the surface of the storage case for communicating data from the at least one medical device to an external computing device, the data communication connector being coupled to the at least one medical device via a second cable; and
   an external computing device for determining a state of readiness of the at least one medical device by determining a charged state of the battery, prompting the medical device to perform system checks of the at least one processor of the medical device and simulating operation of the medical device by operating at least one component of the medical device.

10. The system of claim 9, wherein the external computing device is configured to calibrate the at least one medical device.

11. The system of claim 9, wherein the external computing device is configured to cycle an internal battery of the at least one medical device to optimize the battery's life expectancy.

12. The system of claim 9, wherein the external computing device is configured to generate an alert upon failure of the at least one medical device.

13. The system of claim 9, wherein the external computing device is configured to store at least one monitored parameter of the at least one medical device in a database.

14. The system of claim 9, wherein the external computing device is coupled to the data communication connector via a wireless connection.

15. The system of claim 14, wherein the wireless connection is one of a WiFi connection, Bluetooth connection or cellular connection.

16. A method for monitoring and maintaining critical medical equipment stockpiled for emergency use, comprising:
   providing at least one apparatus comprising: a storage case; at least one electrically powered medical device in the storage case; a rechargeable battery and at least one processor operatively connected to the electrically powered medical device in the storage case; an external power connector disposed on a surface of the storage case for providing power to the at least one medical device without opening of the case, the external power connector being coupled to the at least one medical device via a first cable and being configured for recharging the battery; and a data communication connector disposed on the surface of the storage case for communicating data from the at least one medical device to an external computing device, the data communication connector being coupled to the at least one medical device via a second cable; and
   using the external computing device to determine a charged state of the battery and to prompt the medical device to perform a system check of the at least one processor of the medical device; and using the external computing device to simulate operation of the medical device by operating at least one component of the medical device to determine a state of readiness of the at least one medical device by the external computing device.

17. The method of claim 16, further comprising cycling, by the external computing device, an internal battery of the at least one medical device to optimize the battery's life expectancy.

\* \* \* \* \*